(12) United States Patent
Pescatore et al.

(10) Patent No.: US 7,899,226 B2
(45) Date of Patent: Mar. 1, 2011

(54) SYSTEM AND METHOD OF NAVIGATING AN OBJECT IN AN IMAGED SUBJECT

(75) Inventors: Jeremie Pescatore, Yvelines (FR); Michel F. Grimaud, Montrouge (FR); Gerald L. Beauregard, Stratham, NH (US)

(73) Assignee: General Electric Company, Schenectady, NY (US)

( * ) Notice: Subject to any disclaimer, the term of this patent is extended or adjusted under 35 U.S.C. 154(b) by 839 days.

(21) Appl. No.: 11/695,808

(22) Filed: Apr. 3, 2007

(65) Prior Publication Data

US 2008/0247616 A1 Oct. 9, 2008

(51) Int. Cl.
G06K 9/00 (2006.01)
A61B 6/00 (2006.01)
G01N 23/04 (2006.01)

(52) U.S. Cl. .............................. 382/128; 378/4; 378/62

(58) Field of Classification Search .................. 382/128, 382/129, 130, 131, 132, 133, 134; 378/4, 378/21, 23–27, 40, 62, 63, 87, 98.6, 98.7, 378/901; 600/407, 410, 425, 426; 128/916, 128/920, 922; 701/200
See application file for complete search history.

(56) References Cited

U.S. PATENT DOCUMENTS

| | | | |
|---|---|---|---|
| 5,603,318 A | 2/1997 | Heilbrun et al. | |
| 6,389,104 B1 * | 5/2002 | Bani-Hashemi et al. | 378/98.12 |
| 7,356,367 B2 * | 4/2008 | Liang et al. | 600/407 |
| 7,522,701 B2 * | 4/2009 | Jensen et al. | 378/62 |
| 2002/0198448 A1 | 12/2002 | Zuk et al. | |
| 2004/0097806 A1 | 5/2004 | Hunter et al. | |
| 2005/0281385 A1 | 12/2005 | Johnson et al. | |
| 2006/0258938 A1 | 11/2006 | Hoffman et al. | |

OTHER PUBLICATIONS

French Search Report and Written Opinion issued in connection with corresponding FR Application No. 0852182 on Aug. 30, 2010.

* cited by examiner

Primary Examiner—Abolfazl Tabatabai

(57) ABSTRACT

A system to navigate an image-guided object traveling in an area of interest of an imaged subject in relation to an acquired image of the imaged subject as created by an imaging system is provided. The system includes a navigation system to track movement of the object in the imaged subject in spatial relation to a navigation coordinate system, and a controller. The controller is operable in detecting an image of the object in the at least one image of the imaged subject, calculating a spatial relation between the location of the image of the object and a tracked location of the object, and modifying the spatial relation of the image coordinate system relative to the navigation coordinate system so as to reduce the difference between the location of the image of the object and the tracked location of the object by the navigation system.

20 Claims, 2 Drawing Sheets

SYSTEM AND METHOD OF NAVIGATING AN OBJECT IN AN IMAGED SUBJECT

BACKGROUND OF THE INVENTION

The subject matter herein generally relates to a medical imaging, and more specifically, to a system and method of navigating an object through an imaged subject.

Image-guided surgery is a developing technology that generally provides a surgeon with a virtual roadmap into a patient's anatomy. This virtual roadmap allows the surgeon to reduce the size of entry or incision into the patient, which can minimize pain and trauma to the patient and result in shorter hospital stays. Examples of image-guided procedures include laparoscopic surgery, thoracoscopic surgery, endoscopic surgery, etc. Conventional medical diagnostic imaging tools such as computerized tomography (CT), magnetic resonance imaging (MRI), positron emission tomography (PET), ultrasound, radiological machines, etc. can be useful in providing static image guiding assistance in such procedures. The above-described imaging tools can provide two-dimensional or three-dimensional images that can be displayed to provide a surgeon or clinician with an illustrative map of an area of interest of a patient's body.

Certain navigation systems have been developed for monitoring the position and movement of a surgical instrument or object relative the above-described images. Generally, as a surgeon moves the medical instrument with respect to the patient's anatomy, virtual images of the instrument or object are displayed relative to the acquired images. These certain conventional navigation systems employ the use of passive articulated mechanical arms, electromagnetic detection, optical detection, and ultrasonic detection to track a location of the instrument with respect to the patient's anatomy. Computer programmed algorithms are then employed to track the spatial relationship between the tracked instrument or object and the acquired image.

There is a need for a system and method of tracking to enhance the quality and accuracy in illustrating a tracked location of the object relative to the surrounding anatomical features and structures of the imaged subject.

BRIEF DESCRIPTION OF THE INVENTION

The above-mentioned need is addressed by the embodiments of the subject matter described herein in the following description.

In accordance with one embodiment, a system to navigate an image-guided object traveling in an area of interest of an imaged subject in relation to an acquired image of the imaged subject as created by an imaging system is provided. The spatial relation of the at least one image is defined with respect to an image coordinate system. The system includes a navigation system operable to track movement of the object in the imaged subject, the object tracked in spatial relation to a navigation coordinate system. The system also includes a controller electrically connected in communication with the imaging system and the navigation system. The controller includes a processor operable to execute a plurality of program instructions stored in a memory. The plurality of program instructions are representative of the steps of registering a spatial relation of the imaging coordinate system relative to the navigation coordinate system, detecting an image of the object in the at least one image of the imaged subject, calculating a spatial relation between the location of the image of the object and a tracked location of the object, and modifying the spatial relation of the image coordinate system relative to the navigation coordinate system so as to reduce the difference between the location of the image of the object and the tracked location of the object by the navigation system.

An embodiment of a method of navigating an object through an area of interest of an imaged subject is also provided. The method comprises the steps of registering a spatial relation of an imaging coordinate system relative to a navigation coordinate system, the imaging coordinate system definitive of a spatial relation of at least one image of the imaged subject as acquired by an imaging system, the navigation coordinate system defined by a navigation system configured to track a location of the object in the imaged subject; detecting an image of the object in at least one image of the imaged subject; registering a location of the image of the object relative to the image coordinate system; comparing the location of the image of the object with a tracked location of the object as measured by the navigation system; and displaying a spatial relation between the location of the image of the object and the tracked location of the object.

An embodiment of a system to navigate an image-guided object traveling in an area of interest of an imaged subject is also provided. The system comprises an imaging system, a navigation system, and a controller. The imaging system is operable to acquire at least one image of the imaged subject, a spatial relation of the at least one image defined with respect to an image coordinate system. The navigation system is operable to track movement of the object in the imaged subject, the object tracked in spatial relation to a navigation coordinate system. The controller is connected in communication with the imaging system and the navigation system. The controller includes a processor operable to execute a plurality of program instructions stored in a memory. The plurality of program instructions comprises registering a spatial relation of the imaging coordinate system relative to the navigation coordinate system, detecting an image of the object in the at least one image of the imaged subject, registering a location of the image of the object relative to the image coordinate system, comparing the location of the image of the object with a tracked location of the object as measured by the navigation system, and modifying the spatial relation of the image coordinate system relative to the navigation coordinate system so as to reduce the difference between the location of the image of the object and the tracked location of the object by the navigation system.

Systems and methods of varying scope are described herein. In addition to the aspects and advantages described in this summary, further aspects and advantages will become apparent by reference to the drawings and with reference to the detailed description that follows.

DETAILED DESCRIPTION OF THE INVENTION

Figure 1:
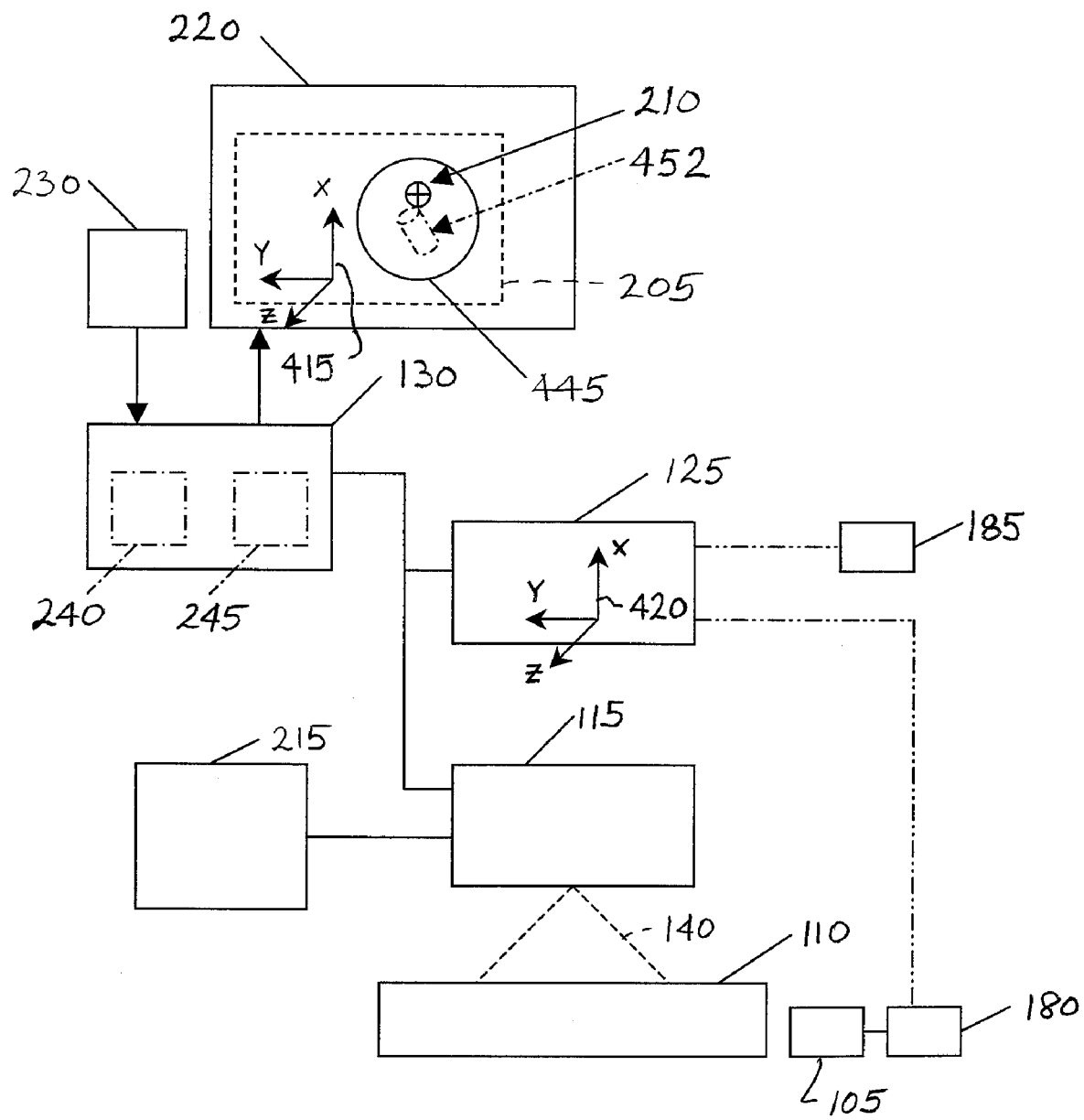
FIG. 1 shows a schematic block diagram illustrative of an embodiment of a system operable to track an object through an anatomy of an imaged subject.

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodi- FIG. 1 illustrates an embodiment of a system 100 operable to track movement of a tool or object 105 through an anatomy of an imaged subject 110. The system 100 generally includes an imaging system 115, a navigation system 125, and a controller 130 connected in communication to track a position of the object 105 traveling through the imaged subject 110. A technical effect of the system 100 is to allow modification of the registration of the imaging system 115 with the navigation system 125 based on a comparison of an identified location of the object 105 in an acquired image relative to the tracked location of the object 105. Thereby, the system 100 enhances an ability to more accurately track movement of the object 105 so as to enable performance of more delicate procedures with reduced likelihood to damage critical surrounding structures such as arteries and nerves.

The imaging system 115 is generally operable to generate the two-dimensional, three-dimensional, or four-dimensional image 135 corresponding to an area of interest of the imaged subject 110. Examples of the type of imaging system 115 can include, but is not limited to, computed tomography (CT), magnetic resonance imaging (MRI), X-ray, positron emission tomography (PET), tomosynthesis, ultrasound, angiographic, fluoroscopic, and the like or combination thereof. The imaging system 115 can be operable to generate static images acquired by static imaging detectors (e.g., CT systems, MRI, etc.) prior to a medical procedure, or real-time images acquired with real-time imaging detectors (e.g., fluoroscopic systems, laparoscopic systems, endoscopic systems, etc.) during the medical procedure. Thus, the types of images can be diagnostic or interventional. In one example, the imaging system 115 includes a static imaging system in combination with a real-time imaging system. In another example, the imaging system 115 is configured to generate a fusion of an image acquired by a CT imaging system with an image acquired by an MR imaging system. This embodiment can be employed in the surgical removal of tumors. The tumor is generally visible in the MR image, and the bone structure is generally visible in the CT image. The acquired image data is communicated directly or indirectly from the imaging system 115 via a communication link to the navigation system 125.

An exemplary imaging system 115 is an X-ray imaging system includes a X-ray generator or source (not shown) operable to pass X-rays 140 through the imaged subject 110, and a detector (not shown) operable to create a diagnostic image. The imaging system 115 can further include a movable support assembly or gantry (not shown) having a mobile arm (e.g., a C-shaped arm, etc.) in mobile support of the x-ray source and detector in relation to the imaged subject 110.

The object 105 can be a tool in combination with an anatomical structural. Examples of tools include surgical tool, navigational tool, a guidewire, a catheter, an endoscopic tool, a laparoscopic tool, ultrasound probe, pointer, aspirator, coil, or the like employed in a medical procedure. Yet, the type of object 105 can vary.

The navigation system 125 is generally operable to track or detect a position of the object 105 relative to the at least one acquired image 135 generated by the imaging system 115. The exemplary navigation system 125 includes an array or series of tracking elements 180 and 185 connected (e.g., via a hard-wired or wireless connection) to communicate position data (See FIG. 1). Yet, it should be understood that the number of tracking elements can vary. An embodiment of the tracking elements 180 and 185 comprises one or more transmitters or dynamic references in electromagnetic communication or electromagnetically coupled with one or more receivers. At least one of the tracking elements 180 and 185 transmits a field of electromagnetic energy (e.g., 10-20 kHz) operable to be detected by at least one other tracking elements 180 and 185. In response to passing through a field of electromagnetic energy, the receiver generates a signal indicative of a special relation to the transmitter. Yet, it should be understood that the type of mode of coupling, link or communication (e.g., rf, infrared light, etc.) operable to measure a spatial relation can vary.

In accordance with one embodiment, the tracking element 180 is attached at the object 105 being tracked traveling through the imaged subject 110. The tracking element 180 can be detachably connected to the object 105 via a snap-on assembly, a slide-in hole, or include some other mechanical connector assembly known in the art. The tracking element 185 is attached at a reference (e.g., the imaged subject 110 the table, the gantry, etc.). One embodiment of at least one of the tracking elements 180 and 185 includes a transmitter having a plurality of coils (e.g., Hemholtz coils) operable to generate an electromagnetic gradient field in the region of interest where tracking is to occur. Another embodiment of at least one of the tracking elements 180 and 185 includes at least one conductive loop operable to generate an electric signal indicative of a position relative to an electromagnetic field generated by one or more of the other tracking elements 180 and 185 in the predetermined work space or region of interest where tracking is to occur.

The navigation system 125 is operable to track movement of the object 105 in accordance to known mathematical algorithms programmed as program instructions of a software. Examples of known navigation software to track movement include INSTATRAK® as manufactured by the GENERAL ELECTRIC® Corporation, the STEALTHSTATION® as manufactured by MEDTRONIC® Corporation, and KOLIBRI® as manufactured by BRAINLAB® Corporation. The exemplary software is also operable to use two- or three-dimensional MRI, CT and/or X-ray acquired image data by the imaging system 115 to build a digitized three-, or four-dimensional anatomical roadmap or model 205 of a patient's anatomy, and electromagnetic (EM) tracking technology that operates as a type of "global positioning system" to show the location of the object 105 in real-time in spatial relation to the anatomical roadmap 205. A representation 210 of the object 105 in spatial relation to the anatomical roadmap 205 can appear on a display 230 of the imaging system 115 or other display 220 of the system 100 to guide the physician during delicate procedures such as Ear, Nose and Throat (ENT), Neurocranial or Spinal surgical procedures. Various types of symbols, such as a cursor, triangle, square, cross-hairs, etc. can be used the representation 210 of the tracked location of the object 105.

Still referring to FIG. 1, the controller 130 is generally connected in communication with each of the tracking elements 180, 185, an input 230, and the display 220 (e.g., monitor, touch-screen, speaker, etc.). The controller 130 can be integrated with either the imaging system 115 and/or the navigation system 125, or be a stand-alone system. An embodiment of the controller 130 generally includes a processor 240 in communication with a memory 245. The processor 240 can be arranged independent of or integrated with the memory 245.

The processor 240 is generally operable to execute the program instructions representative of acts described herein and stored in the memory 245. The processor 240 can also be capable of receiving input data or information from the input 230 or communicating output data for illustration on the display 230. Examples of the processor 240 can include a central processing unit of a desktop computer, a microprocessor, a microcontroller, or programmable logic controller (PLC), or the like or combination thereof.

An embodiment of the memory 245 generally comprises one or more computer-readable mediums such as a hard disk, a floppy disk, CD, CD-ROM, DVD, compact storage medium, flash memory, random access memory, read-only memory, programmable read-only memory, memory stick, or the like or combination thereof. The memory 245 is operable to store the plurality of program instructions for execution by the processor 240, as well as store data generated by the controller 130 and/or received via the input 230 to the controller 130.

The input can include any device operable to receive and communicate information data from user to the controller 130. The input 230 can include a mouse device, pointer, keyboard, touch screen, or other like device capable of receiving a user directive. The input 230 may include capabilities for voice recognition, motion tracking, and/or eye tracking.

The display 230 is generally a device operable to illustrate output data for viewing by the user. The exemplary display 230 is operable to simultaneously illustrate or fuse static or real-time image data generated by the imaging system 115 with tracking data generated by the navigation system 125. The display 230 can include a cathode ray monitor, a liquid crystal display (LCD) monitor, a plasma monitor, or the like or combination thereof. The display 230 is capable of illustrating two-dimensional, three-dimensional image and/or four-dimensional image data through shading, coloring, and/or the like.

Having provided a description of the general construction of the system 100, the following is a description of a method 400 (see FIG. 2) of operating of the system 100 in relation to the imaged subject 110. Although an exemplary embodiment of the method 400 is discussed below, it should be understood that one or more acts or steps comprising the method 400 can be omitted or added. It should also be understood that one or more of the acts can be performed simultaneously or at least substantially simultaneously, and the sequence of the acts can vary. Furthermore, it is embodied that at least several of the following acts can be represented as a series of modules of computer-readable program instructions to be stored in the memory 245 of the controller 130 for execution by the processor 240.

Figure 2:
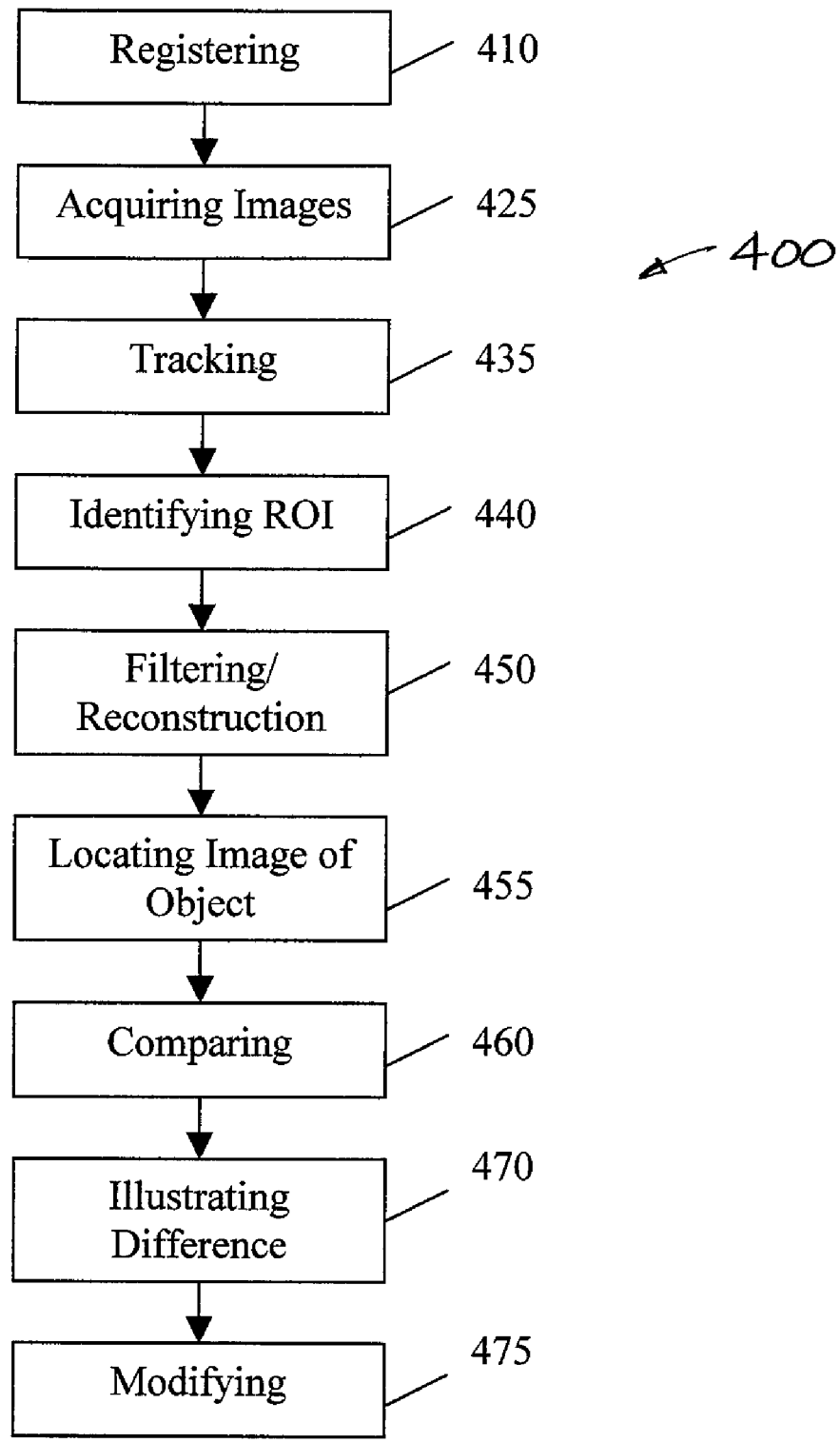
FIG. 2 shows a flow diagram of an embodiment of a method to operate the system in FIG. 1 so as to track the object through the anatomy of the imaged subject.

Assume the tracking element 180 is attached at the object 105, and the other tracking element 185 is attached at a reference (e.g., table, gantry of imaging system 115, imaged subject 110, etc.). Referring now to FIG. 2, act 410 includes initially registering an image coordinate system 415 relative to a navigation coordinate system 420. The controller 130 is operable to automatically register the image coordinate system 415 relative to the navigation coordinate system 420 in a known manner. The registering act 410 can include executing a predetermined registration algorithm in the software described above that was previously acquired or used to automatically register the coordinate systems 415 and 420, or an initial guess of a registration algorithm. An example of act 410 includes locating the tracking elements 180 and 185 relative to images of reference or fiducial markers (not shown) located in a known spatial relation, or images of a phantom (not shown) located in a known spatial relation, or a combination of the above so as to calculate a spatial relation between the image coordinate system 415 of the imaging system 115 and the navigation coordinate system 420 of the navigation system 125, in a known manner.

Act 425 includes acquiring a series of images 135 of the object 105 having been inserted in the imaged subject 110. It should be understood that series of acquired images 135 can include various types of diagnostic images, interventional images, or fusion of images as acquired by various types of the imaging system 115, including the examples described above.

Act 430 includes tracking movement or position of the object 105 in the subject 110. As the object 105 travels with the imaged subject 110, the controller 130 tracks movement of the object 105 in spatial relation relative to the navigation coordinate system 420 for illustration on the display 205, such as in a surgical suite or operating room. The act 430 can include generating a composite image that comprises the representation 210 of the object 105 in spatial relation to the acquired image 135 of the imaged subject 110 as acquired by the imaging system 115.

In one example, the imaging system 115 includes a CT imaging system operable to acquire a CT image scan and an endoscopic imaging system operable to acquire an endoscopic image scan, respectively, the CT and endoscopic image scans illustrated simultaneously or fused together in the anatomical roadmap 205 for illustration on the display 220 while the surgeon moves the object 105 through the imaged subject 110. The navigation system 125 generates the representation 210 (e.g., cross-hairs) of the object 105 for visualization on the anatomical roadmap 205 that includes both the CT image scan and the endoscopic image scan. The system 100 may be used in guiding various objects 105, such as shunts and catheters, or in performing biopsies. The system 100 may also be employed by neurosurgeons in performing cranial surgeries so as to reduce risk to motor, speech, and somato-sensory areas.

Act 440 includes identifying a region of interest (ROI) 445 in one or more acquired images 135 of the imaged subject 110 where to expect or of increased liklihood to find an acquired image 452 of the object 105. An embodiment of act 425 includes calculating and locating an expected location of the object 105 relative to the acquired images 135, as identified in accordance to a tracked location of the object 105 by the navigation system 125 relative to registration with the navigating coordinate system 420 and the imaging coordinate system 415. The act 440 can include superimposing a graphical representation (e.g., a circle, a square, a triangle, or other geometric form) of the ROI 445 surrounding the expected location of the object 105 in one or more of the acquired images 135 of the imaged subject 110.

Act 450 includes performing image filtering (e.g., line filtering) or filtered back-projection or local tomographic reconstruction techniques to increase a contrast of an image 452 of the object 105 relative to other anatomy, anatomical reference markers, or other reference in the acquired image 135 of the imaged subject 110. An embodiment of act 450 includes acquiring a predetermined grayscale value of an image 452 of the object 105 as previously acquired or determined by the imaging system 115. Yet, other known filtering or image reconstruction techniques can be employed so as to increase the contrast of the object 105 in the acquired image 135.

Act 455 includes identifying and measuring a location of the image 452 of the object 105 in the acquired images of the imaged subject 110. Act 440 includes automatically registering the location of the image 452 of the object 105 relative to the image coordinate system and the navigation coordinate system.

Act 460 includes comparing the location of the image 452 of the object 105 relative to the tracked location of the object 105 as measured via the tracking elements 180 and 185 of the navigation system 125. An embodiment of act 460 includes calculating a rigid transformation or registration in the location of the object 105 relative to the tracked location of the image 452 of the object 105 and comparison to a threshold. The difference can include components in rotation or translation or both.

Act 470 includes illustrating the difference in the location of the image 452 of the object 105 and the tracked location of the object 105 in the display for illustration to the operator. An embodiment of act 470 also includes superimposing the representation 210 of the tracked location of the object 105 in spatial relation to the identified or detected location of the image 452 of the object 105 in the acquired image 135. Alternatively, the act 470 can include superimposing the representation 210 of the tracked location of the object 105 in spatial relation to a representation of the detected location of the image 452 of the object 105.

Act 475 includes modifying registration of the imaging coordinate system 415 and the navigation coordinate system 420 relative to one another if outside the threshold. An embodiment of the modifying act 475 includes adjusting the spatial relation of the imaging coordinate system 415 relative to the navigation coordinate system 420 so as cause the identified location of the image 452 of the object 105 in the acquired image 135 to match or correlate with the tracked location of the object 105 in accordance to the navigation system 125, or in other words, so as to reduce the difference between the location of the image 452 of the object 105 and the tracked location of the object 105 by the navigation system 125. Alternatively, act 475 can include modifying the spatial relation of imaging coordinate system 415 relative to the navigation coordinate system 420 by a predetermined or input percentage of the difference described above so as to cause the image 452 of the object 105 in the acquired image 135 to at least better match or correlate with the tracked location of the object 105 in accordance to the navigation system 125.

This written description uses examples to disclose the subject matter, including the best mode, and also to enable any person skilled in the art to make and use the subject matter described herein. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system to navigate an image-guided object traveling in an area of interest of an imaged subject in relation to an acquired image of the imaged subject as created by an imaging system, a spatial relation of the at least one image defined with respect to an image coordinate system, comprising:
   a navigation system operable to track movement of the object in the imaged subject, the object tracked in spatial relation to a navigation coordinate system; and
   a controller electrically connected in communication with the imaging system and the navigation system, the controller having a processor operable to execute a plurality of program instructions stored in a memory, the plurality of program instructions comprising:
      registering a spatial relation of the imaging coordinate system relative to the navigation coordinate system,
      detecting an image of the object in the at least one image of the imaged subject, calculating a spatial relation between the location of the image of the object and a tracked location of the object, and
      modifying the spatial relation of the image coordinate system relative to the navigation coordinate system so as to reduce the difference between the location of the image of the object and the tracked location of the object by the navigation system relative to the image.

2. The system of claim 1, wherein detecting includes identifying a region of interest in the at least one image having increased likelihood of a location of the image of the object.

3. The system of claim 2, wherein detecting includes applying a filter to increase a contrast of the image of the object in relation to a contrast of image of an anatomical structure in the at least one image.

4. The system of claim 1, the plurality of programmable instructions further comprising:
   displaying the spatial relation relative a predetermined threshold.

5. The system of claim 1, the plurality of programmable instructions further comprising:
   displaying the spatial relation between the location of the image of the object and the tracked location of the object.

6. The system of claim 5, wherein displaying includes superimposing the image of the object and a representation of the tracked location of the object.

7. The system of claim 5, wherein displaying includes superimposing a first representation of the location of the image of the object and a second representation of the tracked location of the object.

8. The system of claim 1, wherein modifying includes adjusting the spatial relation of the image coordinate system relative to the navigation coordinate system by a predetermined percentage of the spatial relation.

9. The system of claim 1, wherein the spatial relation includes one or more of the group consisting of rotation and translation.

10. A method of navigating an object through an area of interest of an imaged subject, the method comprising the steps of:
   registering a spatial relation of an imaging coordinate system relative to a navigation coordinate system, the imaging coordinate system definitive of a spatial relation of at least one image of the imaged subject as acquired by an imaging system, the navigation coordinate system defined by a navigation system configured to track a location of the object in the imaged subject;
   detecting an image of the object in at least one image of the imaged subject;
   registering a location of the image of the object relative to the image coordinate system,
   comparing the location of the image of the object with a tracked location of the object relative to the image as measured by the navigation system, and
   displaying a spatial relation between the location of the image of the object and the tracked location of the object relative to the image.

11. The method of claim 10, wherein the detecting step includes identifying a region of interest in the at least one image having increased likelihood of a location of the image of the object.

12. The method of claim 10, wherein the detecting step includes applying a filter to increase a contrast of the image of the object in relation to a contrast of image of an anatomical structure in the at least one image.

13. The method of claim 10, the method further including the step of:

modifying the spatial relation of the image coordinate system relative to the navigation coordinate system so as to reduce the spatial relation between the location of the image of the object and the tracked location of the object by the navigation system.

14. The method of claim 10, wherein the displaying step includes superimposing the image of the object and a representation of the tracked location of the object.

15. The method of claim 10, wherein the displaying step includes superimposing a first representation of the location of the image of the object and a second representation of the tracked location of the object.

16. The method of claim 10, further comprising the step of displaying the spatial relation relative a predetermined threshold.

17. A system to navigate an image-guided object traveling in an area of interest of an imaged subject, comprising:
   an imaging system operable to acquire at least one image of the imaged subject, a spatial relation of the at least one image defined with respect to an image coordinate system;
   a navigation system operable to track movement of the object in the imaged subject, the object tracked in spatial relation to a navigation coordinate system; and
   a controller electrically connected in communication with the imaging system and the navigation system, the controller having a processor operable to execute a plurality of program instructions stored in a memory, the plurality of program instructions comprising:
      registering a spatial relation of the imaging coordinate system relative to the navigation coordinate system,
      detecting an image of the object in the at least one image of the imaged subject, registering a location of the image of the object relative to the image coordinate system,
      comparing the location of the image of the object with a tracked location of the object relative to the image as measured by the navigation system, and
      modifying the spatial relation of the image coordinate system relative to the navigation coordinate system so as to reduce the difference between the location of the image of the object and the tracked location of the object by the navigation system relative to the image.

18. The system of claim 17, wherein detecting includes:
   identifying a region of interest in the at least one image having increased likelihood of a location of the image of the object, and
   filtering the region of interest to increase a contrast of the image of the object in relation to a contrast of image of an anatomical structure in the at least one image.

19. The system of claim 17, the plurality of program instructions comprising:
   displaying the spatial relation between the location of the image of the object and the tracked location of the object.

20. The system of claim 19, wherein displaying includes superimposing a first representation of the location of the image of the object and a second representation of the tracked location of the object.

* * * * *